United States Patent [19]

Haslwanter et al.

[11] Patent Number: 4,963,359

[45] Date of Patent: Oct. 16, 1990

[54] NON-CARIOGENIC CONFECTIONS

[75] Inventors: Joseph Haslwanter, Germantown; Walter G. Chambliss, Cordova, both of Tenn.

[73] Assignee: Plough, Inc., Memphis, Tenn.

[21] Appl. No.: 303,794

[22] Filed: Jan. 30, 1989

[51] Int. Cl.$^5$ ................................................ A61K 9/20
[52] U.S. Cl. ................................... 424/440; 424/439; 424/441; 424/464; 424/465
[58] Field of Search ............... 424/440, 441, 439, 464, 424/465

[56] References Cited

U.S. PATENT DOCUMENTS

| | | | |
|---|---|---|---|
| Re. 26,959 | 9/1970 | Conrad | 99/141 |
| 2,926,121 | 2/1960 | Hobbs et al. | 424/440 |
| 3,456,050 | 7/1969 | Rieckmann et al. | 424/440 |
| 3,556,811 | 1/1971 | Smith | 99/134 |
| 3,697,641 | 10/1972 | Ahrens | 424/440 |
| 4,279,931 | 7/1981 | Verwaerde et al. | 426/43 |
| 4,323,588 | 4/1982 | Vink et al. | 426/564 |
| 4,346,168 | 8/1982 | Verwaerde et al. | 426/48 |
| 4,382,962 | 5/1983 | Devos et al. | 426/3 |
| 4,528,206 | 7/1985 | Kastin | 426/660 |
| 4,548,806 | 10/1985 | Colliopoulos et al. | 424/440 |
| 4,597,981 | 7/1986 | Kastin | 426/660 |
| 4,714,620 | 12/1987 | Bunick | 426/572 |
| 4,857,331 | 8/1989 | Shaw et al. | 424/440 |

*Primary Examiner*—Thurman K. Page
*Attorney, Agent, or Firm*—Thomas D. Hoffman; John J. Maitner; Gerald S. Rosen

[57] ABSTRACT

A non-cariogenic confectionery base free of cellulosics and graining compounds containing hydrogenated starch hydrolysates e.g. Lycasin 85%, more than 10 to about 50% by weight of at least one edible oil, fat, wax or mixtures thereof and an emulsifying amount of at least one emulsifier and a method of making same are disclosed. A non-cariogenic confectionery composition containing said confectionery base in homogeneous admixture with a semi-solid matrix containing various ingredients and optionally at least one medicament is also disclosed.

6 Claims, No Drawings

NON-CARIOGENIC CONFECTIONS

BACKGROUND OF THE INVENTION

This invention relates to a non-cariogenic confectionery base containing a homogeneous admixture of hydrogenated starch hydrolysates, at least one emulsifier and about 10 to about 25 weight percent of at least one edible fat, oil, wax or mixtures thereof. This invention also relates to non-cariogenic confectionery compositions containing such non-cariogenic confectionery bases in homogeneous admixture with a semi-solid matrix containing various ingredients and optionally containing at least one medicament. Methods of making such non-cariogenic confectionery bases and compositions are also disclosed.

The term "confectionery compositions" as used herein means hard candies or lozenges, semi-hard candies, semi-soft candies, and soft chew candies such as nougats. Confectionery bases have been used to form confectionery compositions or candies as well as medicated confectionery compositions for administration of pharmaceutical compositions.

Confectionery bases and compositions were previously based on fermentable carbohydrates such as sucrose and/or corn syrup. A number of non-fermentable carbohydrates such as sorbitol have been developed to produce sugarless non-cariogenic confectionery compositions. Of particular interest is hydrogenated starch hydrolysates available under the tradename Lycasin ® from Roquette, Freres, France and disclosed in U.S. Pat. No. 4,346,116.

Unfortunately, hydrogenated starch hydrolystates are hydroscopic and generally form confections that are relatively unstable under high temperatures (e.g. 80° F. or higher) and high relative humidity conditions (e.g. 80% relative humidity or higher). U.S. Pat. Nos. 4,528,206 and 4,597,981 disclose that soft confectionery compositions containing hydrogenated starch hydrolysates tend to become sticky, and both hard and soft confectionery compositions containing hydrogenated starch hydrolysates have a tendency to cold flow and to become sticky when subjected to such high temperature and high relative humidity conditions.

To overcome this cold flow problem, careful wrapping of confectionery compositions under controlled temperature, humidity conditions has been tried. U.S. Pat. Nos. 4,597,981 and 4,528,206 disclose incorporation into such confectionery compositions a substantial amount of a polymer of glucose or maltose to overcome the problem of cold flow. U.S. Pat. No. 4,323,588 discloses that sugarless confections such as marshmallow and nougat types containing Lycasin ® and hydrogenated sugars may be produced. Hydrogenated sugars, however, such as isomaltitol and isomaltulose are very expensive and not readily available. U.S. Pat. No. 4,714,620 discloses that the incorporation of cellulosics (a specific ratio of water soluble and water insoluble cellulosics) reduces the inherent excessive cold flow and stickiness associated with confections containing hydrogenated starch hydrolysates.

All these procedures and additives add to the time and cost of preparing the confectionery compositions.

There is a need for a relatively simple, inexpensive way to produce non-cariogenic confectionery compositions containing hydrogenated starch hydrolysates that can be cut and wrapped using equipment well known in the confectionery industry.

SUMMARY OF THE INVENTION

We have discovered a simple and efficient method, using cooking and mixing equipment well known in the confectionery and pharmaceutical arts, to make a wide range of sugarless, non-cariogenic confectionery bases and compositions (from hard lozenges to soft chewy nougats) which may contain up to about 50% by weight of one or more medicaments. Briefly stated, we have discovered that by incorporating a larger amount (i.e. more than the 10 weight percent of total fat disclosed in U.S. Pat. 4,714,620) than previously thought possible of at least one edible fat, oil, wax or mixtures thereof with an emulsifier and hydrogenated starch hydrolysates and cooking the mixture until a homogeneous admixture is formed, there is produced a confectionery base called a viscous liquid matrix. When the viscous liquid matrix is homogeneously admixed or blended with a semi-solid matrix containing various ingredients and optionally including for example at least one medicament, there is produced an uniform medicated confectionery composition with a desirable (i.e., smooth and pleasant) mouthfeel. Furthermore, the cold flow problems associated with other confectionery compositions containing hydrogenated starch hydrolysates have been substantially reduced. No cellulosics, graining compounds or expensive ingredients such as isomultitol or isomultulose are used to make the non-cariogenic confectionery compositions of this invention.

Thus, this invention provides a non-cariogenic confectionery base, free of cellulosics and graining compounds, said base comprising a homogeneous admixture of:

(a) hydrogenated starch hydrolysates;

(b) at least one edible fat, oil wax or mixtures thereof in an amount in the range of more than 10 to about 50 weight percent of said base; and (c) about 0.5 to about 3 weight percent of water; and (d) at least one emulsifier in an amount sufficient to emulsify the homogeneous admixture.

This invention also provides a method of making a non-cariogenic confectionery base which comprises admixing an aqueous solution of about 50 to about 90 parts by weight of hydrogenated starch hydrolysates, more than 10 to about 50 parts by weight of at least one edible fat, oil, wax or mixtures thereof and at least one emulsifier in an amount sufficient to emulsify said confectionery base to a temperature in the range of about 120° C. to about 180° C. for a time sufficient to obtain a non-cariogenic confectionery base as a homogeneous admixture containing about 50 to about 90 parts by weight of hydrogenated starch hydrolysates, more than 10 to about 50 parts by weight of at least one edible fat, oil wax or mixtures thereof and said emulsifying amount of at least one emulsifying agent and having a water content of about 0.5 to about 3 weight percent of said base and being free of cellulosics and graining compounds.

This invention also provides a non-cariogenic confectionery composition free of cellulosics and graining compounds, said composition comprising:

(a) a viscous liquid matrix, in an amount from about 50% to about 99% by weight of said composition, which comprises:

(1) hydrogenated starch hydrolysates;

(2) at least one emulsifier in an amount sufficient to emulsify the viscous liquid matrix; and (3) at least one edible fat, oil, wax or mixtures thereof in an amount of more than 10% to about 50% by weight of said composition;

in homogeneous admixture with (b) a semi-solid matrix in an amount from about 50% to about 1% by weight of said composition, said semi-solid matrix comprising:
  (1) hydrogenated starch hydrolysates in an amount of about 0% to about 75% by weight of said semi-solid matrix;
  (2) at least one humectant;
  (3) at least one viscosity-enhancer; and
  (4) about 0.5 to about 8 weight percent water in said confectionery composition.

This invention further provides a medicated non-cariogenic confectionery composition free of cellulosics and graining compounds said composition comprising:

(a) a viscous liquid matrix in an amount from about 50% to about 99% by weight of said confectionery composition; said viscous liquid matrix comprising:
  (1) hydrogenated starch hydrolysates in an amount of about 50% to about 95% by weight of said viscous liquid matrix;
  (2) at least one emulsifier in an amount of about 0.5% to about 5% of said viscous liquid matrix;
  (3) at least one edible fat, oil, wax, or mixtures thereof in an amount of more than 10% to about 50% by weight of said viscous liquid matrix and more than 10% to about 25% by weight of said confectionery composition;

in homogeneous admixture with (b) a semi-solid matrix in an amount from about 50% to about 1% by weight of said confectionery composition, said semi-solid matrix comprising:
  (1) hydrogenated starch hydrolysates, in an amount of about 0% to about 75% by weight of said semi-solid matrix;
  (2) at least one humectant in an amount of about 10% to about 40% by weight of said semi-solid matrix;
  (3) at least one viscosity-enhancer in an amount of about 0.5% to about 10% by weight of said semi-solid matrix;
  (4) at least one medicament in an amount of from about 0.0001% to about 50% by weight of said semi-solid matrix; and
  (5) water in an amount of from about 0.5% to about 8% by weight of said confectionery composition.

This invention also provides a non-cariogenic hard lozenge-type textured confectionery composition free of cellulosics and graining compounds, said composition comprising:

(a) a viscous liquid matrix in an amount from more than 95% to about 99% by weight of said composition, said viscous liquid matrix comprising:
  (1) hydrogenated starch hydrolysates;
  (2) at least one emulsifying agent in an amount sufficient to emulsify the viscous liquid matrix; and
  (3) at least one edible fat, oil, wax or mixtures thereof in an amount of more than 10% by weight to about 26.5% by weight of said viscous liquid matrix and more than 10% to about 25% by weight of said confectionery composition;

in homogeneous admixture with (b) a semi-solid matrix in an amount from less than 5% to about 1 by weight of said composition, said semi-solid matrix comprising:
  (1) hydrogenated starch hydrolystates in an amount of about 0 to about 75% by weight of said semi solid matrix;
  (2) at least one humectant; and
  (3) at least one viscosity-enhancer,
  (4) less than about 1% by weight of water.

This invention further provides a medicated non-cariogenic hard lozenge-type textured confectionary composition free of cellulosics and graining compounds, said composition comprising:

(a) a viscous liquid matrix in an amount from about 95% to about 99% by weight of said composition, said viscous liquid matrix comprising,
  (1) hydrogenated starch hydrolysates;
  (2) at least one emulsifying agent in an amount of about 0.5% to about 5% by weight of said viscous liquid matrix; and
  (3) at least one edible fat, wax, oil or mixtures thereof in an amount of more than 10% to about 26.5% by weight of said viscous liquid matrix and more than 10% to about 25% of said confectionery composition.

in homogeneous admixture with (b) a semi-solid matrix in an amount from about 1% to about 5% by weight of said composition; which comprises:
  (1) hydrogenated starch hydrolysate in an amount of about 0% to about 75% by weight of said semi-solid matrix;
  (2) at least one humectant in an amount of about 10% to about 40% by weight of said semi solid matrix;
  (3) at least one viscosity-enhancer in an amount of about 0.5% to about 10% by weight of said semi-solid matrix;
  (4) at least one medicament in an amount of from about 0.0001% to about 50% by weight of said semi solid matrix; and
  (5) water in an amount of from about 0.5% to less than about 1% by weight of said confectionery composition.

Finally, this invention still further provides a method of preparing a non-cariogenic confectionery composition free of cellulosics and graining compounds, said method comprising the steps of:

(a) producing a homogeneous liquid phase by admixing (1) a solution of about 50 to about 90 parts by weight of hydrogenated starch hydrolysates in water, (2) more than 10 to about 50 parts by weight of at least one edible fat, oil, wax or mixtures thereof, and (3) at least one emulsifier in an amount sufficient to produce a homogeneous liquid phase.

(b) heating the so-produced homogeneous liquid phase to a temperature in the range of about 120° C. to about 180° C. to form a homogeneous viscous liquid matrix wherein the amount of water in said viscous liquid matrix is no more than about 3% by weight and the amount of the at least one edible fat, oil, wax or mixture thereof added is in the range of more than 10% to about 50% by weight of said viscous liquid matrix;

(c) producing a homogeneous admixture by admixing (1) a solution of a hydrogenated starch hydrolysates, if present, in water, (2) at least one humectant, and (3) at least one viscosity-enhancer to form a homogeneous admixture;

(d) heating the homogeneous admixture of step (c) to a temperature in the range of about 20° C. to about 150° C. until a homogeneous semi-solid matrix having a water content in the range of about 1% to about 8% is formed; and (e) admixing from about 50 parts to about 99 parts by weight of said viscous liquid matrix formed in step (b) and from about 1 part to about 50 parts by weight of said homogeneous semi-solid matrix formed in step (d) to form a homogeneous non-cariogenic confectionery composition containing more than 10% to about 25% by weight of said at least one edible fat, oil, wax or mixtures thereof and having a water content in the range of 0.5 to about 8% by weight and being free of cellulosics and graining compounds.

DETAILED DESCRIPTION OF THE INVENTION

The non-cariogenic confectionery bases of this invention contain hydrogenated starch hydrolysates as the bulking agent, at least one edible fat oil, wax or mixtures thereof, an emulsifier in an amount sufficient to emulsify the ingredients in said bases as well as optional ingredients such as colorants, preservatives, edible acids and flavoring agents.

The confectionery base, also called a viscous liquid matrix, is homogeneously admixed with a semi-solid matrix to form a non-cariogenic confectionery composition as an homogeneous product. The semi-solid matrix contains hydrogenated starch hydrolysates, if present, at least one humectant at least one viscosity-enhancer, at least one medicament if present, flavoring agents and colorants, especially pigments.

While this invention is not limited to theoretical consideration, we believe that the heating of a admixture of hydrogenated starch hydrolysates in water, at least one edible fat, wax, oil or mixtures thereof with an emulsifier in accordance with this invention produces a oil-in-water emulsion which, when cooled, forms a homogeneous admixture called a "viscous liquid matrix" or a non-cariogenic confectionary base. It is further believed the formation of this oil-in-water emulsion imparts the desirable mouthfeel to the non-cariogenic confection compositions of this invention and eliminates the processing difficulties associated with prior art products.

The term "non-cariogenic" confectionery base and composition as used herein means a confectionery base or composition substantially free (i.e. containing less than 1% by weight and preferably less than 0.2% by weight) of fermentable sugars such as glucose, and cornsyrup which cause dental caries.

We have discovered a solution that substantially reduces the problem of cold flow and excessive stickiness associated with hydrogenated starch hydrolysate-containing confectionery products by homogeneous admixing at a temperature in the range of about 120° to 180° C. of a solution of about 50 to about 90 parts by weight of hydrogenated starch hydrolysates with more than 10 to about 50 parts by weight of at least one edible fat, wax, oil or mixtures thereof in the presence of an emulsifying agent in an amount sufficient to emulsify the components and produce a non-cariogenic confectionery base. The non-cariogenic confectionery bases and compositions of this invention thereby possess a desirable mouthfeel and are prepared by a simple method without the processing difficulties or incorporation of cellulosics and graining compounds of the prior art.

Thus, it is a special feature of this invention that the non-cariogenic confectionery bases and compositions of this invention are free of, i.e. contain no, graining compounds such as the crystalline sugar alcohols, mannitol, xylitol, sorbitol and the like; prior art confectionery compositions such as disclosed in U.S. Pat. No. 4,714,620 require such graining compounds to be present. The term "graining compounds" means substances added in the form of crystalline solids to promote crystallization, i.e. act as a seeding compound and to control crystal size, in the confectionery products.

It is another special feature of this invention that the confectionery bases and compositions of this invention are free of, i.e., contain no, cellulosics.

The term "cellulosics" (also called cellulose gums) means (a) water-soluble cellulosics which include cellulose polymers and cellulose derivatives such as methylcellellulose, hydroxypropylmethyl cellulose, sodium carboxymethyl cellulose, hydroxyethyl cellulose, hydroxypropyl cellulose, and (b) water-insoluble cellulosics which include powdered cellulose, purified cellulose, alpha cellulose and microcrystalline cellulose.

The present invention provides a range of non-cariogenic confectionery compositions having a wide variety of chewing textures and hardness, e.g. soft chew candies, semi-soft, semi-hard and hard candies or lozenges, to suit a particular medicament or application. Such products are prepared by the homogeneous blending of about 50% by weight to about 99% by weight, preferably about 65% by weight to about 99% by weight, more preferably about 75% by weight to about 99% by weight of the viscous liquid matrix (the non-cariogenic confectionery base) and 50% by weight to about 1%, preferably about 35% by weight to 1% by weight, more preferably about 25% by weight to about 1% by weight of a semi-solid matrix; each of the matrices have been cooked, prior to admixing, to remove a sufficient amount of water to produce a final water content in the range of about 0.5 to about 8 weight percent of the confectionery composition.

The hard-type product or lozenge having a final water content of about 0.5% to less than about 1% may be prepared by homogeneous admixing more than 95% to about 99% of the viscous liquid matrix with less than 5% to about 1% by weight of the semi-solid matrix.

The hard lozenge-type confectionery compositions of the present invention contain more than 10% to about 25% of at least one edible oil, fat, wax or mixtures thereof, preferably about 12 to about 15 percent by weight of a mixture of an edible oil and a wax such as carnauba wax or beeswax. Another preferred medicated lozenge confectionery composition of this invention containing about 12 to 15 percent by weight of beeswax or carnauba wax more slowly dissolves and releases the medicament to provide a longer duration of the medicament than possible with a lozenge having less than 10% by weight of an edible fat, wax or oil.

The semi-hard type confectionery compositions having a final water content of about 1.5% to about 2.5% by weight, preferably about 2% by weight of the final composition are prepared by homogeneous admixing of more than about 85% to about 95% by weight of the viscous liquid matrix with less than about 15% to about 5% by weight of the semi-solid matrix.

The semi-soft type confectionery compositions of the present invention have a final water content of about 2.5% to about 3.5%, preferably about 3% by weight of the final confectionery composition and are prepared by homogeneous admixing of about 75 weight percent to about 85 weight percent of the viscous liquid matrix and about 25% to about 15% by weight of the semi-solid matrix.

The soft type confectionery compositions of this invention have a final water content of about 3.5% to about 8%, preferably about 3.5% to about 6%, more preferably about 4% by weight of the final composition and are prepared by homogeneous admixing of more than about 50% to less than about 75% by weight, preferably about 65% to less than about 75% by weight of the viscous liquid matrix with more than about 25% less than about 50% of the semi-solid matrix preferably more than about 25% to about 35% by weight of the semi-solid matrix.

In one embodiment of this invention, the viscous liquid matrix is prepared by admixing an aqueous solution of about 50 to about 90 parts hydrogenated starch hydrolysates, more than 10 to about 50 parts of at least one edible fat, oil, wax or mixtures thereof with an emulsifying amount i.e. about 0.5 parts to about 5 parts by weight of an emulsifier such as glyceryl monostearate. The admixture is cooked with stirring until a final temperature in the range of about 120° C. to about 180° C. is achieved to form a homogeneous emulsion having a final water content of about 0.5 to about 3 weight percent is produced. To produce a final water content of about 0.5% to about 1% by weight, the viscous liquid matrix is heated until a final temperature of about 160° C. is achieved; to produce a final water content of about 1% to about 3% by weight the viscous liquid matrix is heated until a final temperature of about 140° C. is produced. About 50 parts to about 99 parts by weight of this homogeneous admixture called a viscous liquid matrix is homogeneously admixed with about 50 parts to about 1 part by weight of the semisolid matrix.

The hydrogenated starch hydrolysates may be used in both non-cariogenic confectionery matricies, i.e. the viscous liquid matrix, and the semi-solid matrix. The viscous liquid matrix may contain about 50% to about 95% by weight hydrogenated starch hydrolysates and the semi-solid matrix may contain about 0% to about 75% by weight of hydrogenated starch hydrolysates. The precise amounts of hydrogenated starch hydrolysates used in each matrix depends upon, *inter alia,* the type of confectionery product desired.

Preferred ranges for each type are given in Table I

TABLE I

| Hydrogenated Starch Hydrolysates Content (Weight Percent) | | |
|---|---|---|
| Confectionery type | VSM[1] | SSM[2] |
| Hard | 83% | 0-1% |
| Semi-Hard | 77% | 4% |
| Semi-Soft | 70% | 7% |
| Soft | 56% | 16% |

[1]Viscous Liquid Matrix
[2]Semi-Solid Matrix

The semi-solid matrix containing up to 75 weight percent hydrogenated starch hydrolysates is prepared by the following procedure. The aqueous solution of hydrogenated starch hydrolysates is cooked, with stirring, until a final temperature in the range of about 125° C. to 150° C. is achieved to form a cooked hydrogenated starch hydrolysates having a final water content in the range of about 1% to about 8% by weight. To the cooked hydrogenated starch hydrolysates, there is added, with stirring, at least one humectant, at least one viscosity-enhancer and optionally at least one medicament to form the semi-solid matrix as a homogeneous admixture. To produce a semi-solid matrix having a final water content of about 1% by weight, the cooking is continued until a final temperature of 150° C. is achieved, to obtain a semi-solid matrix having a final water content of about 3.5% by weight, the cooking is continued until a final temperature of about 125° C. is achieved.

The semi-solid matrix containing 0% by hydrogenated starch hydrolysates is prepared by admixing at a temperature in the range of about 20° C. to about 40° C., preferably about 25° C., at least one humectant, at least one viscosity enhancer and optionally at least one medicament to form the semi-solid matrix as a homogeneous admixture.

In one preferred embodiment of this invention an admixture of 89.00 parts by weight of an aqueous solution of 85 weight percent of hydrogenated starch hydrolylsates (Lycasin 85%) in water, 10.57 parts by weight of partially hydrogenated vegetable oil and 0.43 parts by weight of glyceryl monostearate is heated at a temperature in the range of 160° to 165° C. to produce a homogeneous admixture in the form of a water-in-oil emulsion containing 86.90 parts by weight of hydrogenated starch hydrolysates, 13.97 parts by weight of partially hydrogenated vegetable oil, 0.57 parts by weight of glyceryl monostearate and 0.57 parts by weight of water. About 50 to about 99 parts by weight of this homogeneous admixture called a viscous liquid matrix is homogeneously admixed with about 50 parts to about 1 part by weight of the semi-solid matrix to form a non-cariogenic confectionery composition.

In another preferred embodiment of this invention, an admixture of 53.55 parts by weight of an aqueous solution of 85 weight percent of hydrogenated starch hydrolylsates, 45.98 parts by weight of partially hydrogenated vegetable oil and 0.46 parts by weight of glyceryl monostearate is heated at a temperature in the range of 160° to 165° C. to produce a homogeneous admixture in the form of a water-in-oil emulsion containing 49.0 parts by weight of hydrogenated starch hydrolylsates, 50 parts by weight of partially hydrogenated vegetable oil, 0.5 parts by weight of glyceryl monostearate and 0.5 parts by weight of water. About 50 parts to about 99 parts by weight of this homogeneous admixture, called the viscous liquid matrix may be homogeneously admixed with about 50 to about 1 part by weight of the semi-solid matrix to form non-cariogenic confectionery compositions of this invention.

The uncooked hydrogenated starch hydrolysates which may be used to form the cooked hydrogenated starch hydrolysates used in the composition of the present invention may be a hydrogenated corn syrup or hydrogenated starch hydrolysate of varying dextrose equivalents (DE), such as are disclosed in U.S. Pat. No. Re. 26,959 and U.S. Pat. Nos. 3,556,811, 4,279,931 and 4,382,962, as well as various hydrogenated glucose syrups and/or reconstituted powders which contain sorbitol, hydrogenated disaccharides, tri- to hexahydrogenated saccharides, and hydrogenated higher polysaccharides, or mixtures of any two or more of the above.

The uncooked hydrogenated glucose syrups or hydrogenated starch hydrolysates and/or powders thereof may be produced by catalytic hydrogenation of standard glucose syrups (acid and/or enzyme converted) to the point where all the glucose end groups of the saccharides are reduced to alcohols, that is, dextrose to sorbitol. In the case of hydrogenated glucose syrups, the total solids contents will usually range from about 65% to about 85%, which solids are made of from about 4% to 70%, and preferably from about 4% to about 20% by weight of sorbitol from about 8 to about 65%, and preferably from about 20 to about 65% by weight of hydrogenated disaccharides (that is, mannitol), and 20% to 80% of the higher (e.g., tri- to hepta-) hydrogenated saccharides. The preferred the uncooked commercially available hydrogenated starch hydrolysates contain from about 8% to about 45%, and preferably about 15% to 45% by weight of tri- to hepta-hydrogenated saccharides, and from about 10 to about 35%, and preferably about 15% to 25% by weight of hydrogenated saccharides higher than hepta.

The preferred hydrogenated starch hydrolysates for the present invention are the commercially available hydrogenated starch hydrolysates which are referred to in the literature as hydrogenated glucose syrup, and 0 available under the tradename Lycasin® polyol from the Roquette Corporation, Hackensack, N.J. 07601 or available under the tradename Hystar® polyol from The Lonza Corp. Fair Lawn, N.J.. The term "hydrogenated starch hydrolysates" will be used hereinafter to designate such material.

Typical suitable edible oils and fats include hydrogenated and partially hydrogenated vegetable oils, animal oils, vegetable or animal fats such as coconut oil, palm kern oil, beef tallow, lard and cocoa butter. Edible fats are solids at ambient temperatures and edible oils are in the liquid state at ambient temperatures. The preferred edible oil is partially hydrogenated vegetable oil.

The term "edible wax" used herein refers to a low-melting organic mixture or compound of high molecular weight, solid at room temperature and generally similar in composition to fats and oils except that it contains no glycerides. Some are hydrocarbons; others are esters of fatty acids and alcohols. Waxes are thermoplastic, but since they are not high polymers, they are not considered in the family of plastics. Common properties of waxes are water repellency smooth texture, nontoxicity freedom from objectionable odor and color.

Edible waxes are combustible, have good dielectric properties, are soluble in most organic solvents and insoluble in water. The major types of edible wax are as follows:

I. Natural

1. Animal: beeswax, spermaceti, lanolin, shellac wax.
2. Vegetable: carnauba, candelilla, bayberry wax.
3. Mineral
(a) Fossil or earth waxes: ozocerite, ceresin
(b) Petroleum waxes: paraffin, microcrystalline wax.

II. Synthetic

1. Ethylenic polymers and polyol etheresters polyethylene glycol sorbitol
2. Hydrocarbon type via Fischer-Tropsch synthesis having the formula $C_nH_{(2n+2)}$.

In a preferred embodiment, the edible wax is selected from the group consisting of carnauba wax, candelilla wax, paraffin, castor wax, beeswax, stearic acid, stearyl alcohol, cetyl alcohol, esters of fatty alcohols and mixtures thereof. Most preferably the edible wax is selected from the group consisting of carnauba wax, candelilla wax, paraffin, castor wax, beeswax and mixtures thereof.

The edible oil, fat, wax or mixtures thereof make up more than 10 to about 25 weight percent preferably more than 10 to about 15 percent by weight of the non-cariogenic confectionery composition and more than about 10 to about 50.0 percent by weight of the viscous liquid matrix or confectionery bases of this invention. In a preferred embodiment of this invention about 10 to 13 percent by weight of a mixture 77 percent by weight of hydrogenated vegetable oil and 23% by weight of beeswax is used.

Typical suitable emulsifiers include lecithin, mono-, di- and tri-glycerides of $C_{16}$–$C_{20}$ fatty acids especially monoglycerides of fatty acids such as glyceryl monostearate. Other suitable emulsifiers include all emulsifiers approved for internal use that permit homogeneous admixing under conditions of the process of this invention of edible fats, oils and waxes and hydrogenated starch hydrolysates with water to produce uniform, stable emulsions and suspensions. An emulsifying effective amount of an emulsifier useful in this invention is in the range of about 0.5% to about 15 percent by weight, preferably about 0.5% to about 5% by weight of the final confectionery composition. The precise amount of emulsifier depends upon emulsifier used, the weight percent of edible fats, oils and waxes used and the water content of the confectionery composition or base.

The viscous liquid matrix may also contain one or more edible acids. The use of edible acids to provide a tart flavor is well known in the art. Typical suitable edible acids include citric, isocitric, maleic, adipic, tartaric acid and mixtures thereof. Such edible acids may constitute from about 0 to about 5% by weight of the final confectionery composition and are added to the homogeneous admixture of the cooked viscous liquid matrix and uncooked or cooked semi-solid matrix or to either matrix when the temperature of the homogeneous admixture or component is below 100° C. and preferably is about 90° to 95° C.

Typical suitable flavoring agents include natural, artificial and combinations thereof such as peppermint, menthol, chocolate, cinnamon, spearmint, vanilla and various fruit flavors e.g. cherry. The flavoring agent(s) are used in amounts that vary depending upon the individual flavor and range from about 0.5% to about 5% by weight of the final product. Typically the flavoring agent(s) is added to the homogeneous admixture of the cooked viscous liquid matrix and the cooked or uncooked semi-solid matrix when the temperature of the homogeneous admixture is below 100° C., and preferably is in the range of about 90° to about 95° C.

Humectants are used in the confectionery arts to reduce moisture loss, control texture and other desirable characteristics such as mouth feel in the final product. Typical suitable humectants include glycerin, an aqueous solution of sorbitol, protective colloids and mixtures thereof. The preferred humectant is glycerin.

The viscosity-enhancers include at least one gum, hydrocolloid, egg albumin, gelatin, or vegetable proteins such as soy derived compounds and are used in the composition and process of this invention to reduce moisture, control texture, provide a thickening and/or gelling effect. Typical suitable hydrocolloids are long-chain, high-molecular weight polymers that disperse in water to give a thickening and sometimes a gelling effect. Both natural and synthetic hydrocolloids are useful in the present invention. Natural gums are derived from various plant and animal sources. Illustrative, non-limiting examples of natural hydrocolloids suitable for use in the present invention include plant exudates such as arabic, tragacanth, karaya, ghatti; seaweed extracts such as agar, alginates, carrageenans, furcellaran; plant seed gums such as guar, locust bean, psyllium, quince, tamarind; non-fermentable cereal gums such as corn hull gum; plant extracts such as pectin, arabinogalactan; and fermentation gums such as dextran, xanthan and curdlan. Synthetic hydrocolloids or synthetic gums are gum-like chemically synthesized polymers having no structural relationships to natural gums. Illustrative non-limiting examples of synthetic hydrocolloids suitable for food include polyvinylpyrrolidone, carboxyvinyl polymers, and polyethylene oxide polymers. See also Leon Lachman, Herbert A. Lieberman, and Joseph L. Kanig, *The Theory and Practice of Industrial Pharmacy*, Third Edition, Lea and Febiger, Philadelphia, Penna. 1986, p. 518.

The viscosity-enhancers may be used individually or in mixtures. Typically, a mixture of viscosity-enhancers such as egg albumin and gelatin are used. The amount of the viscosity-enhancers varies from about 0.5 to about 10 weight percent of the semi-solid matrix.

The medicament drug may be selected from a wide range of therapeutic agents and mixtures of therapeutic agents. Nonlimiting illustrative categories and specific examples include:

(a) Analgesics, such as acetaminophen, ibuprofen, and salicylamide;

(b) Antiasmatics, such as metaproterenol, and theophylline;

(c) Antitussives, such as dextromethorphan, dextromethorphan hydrobromide, noscapine, carbetapentane citrate, and chlophedianol hydrochloride;

(d) Antihistamines, such as chlorpheniramine maleate, phenindamine tartrate, pyrilamine maleate, doxylamine succinate, phenyltoloxamine citrate, diphenhydramine hydrochloride, promethazine, and triprolidine;

(e) Antinauseant, such as dimenhydrinate, and meclizine;

(f) Decongestants, such as phenylephrine hydrochloride, phenylpropanolamine hydrochloride, pseudoephedrine hydrochloride, ephedrine;

(g) Various alkaloids, such as codeine phosphate, codeine sulfate and morphine;

(h) Laxatives and vitamins, such as phenolphthalein, danthron, and bisocadyl;

(i) Anti-cholesterolemic and anti-lipid agents such as gemfibrozil;

(j) Appetite suppressants such as phenylpropanolamine hydrochloride, and caffeine;

(k) Central nervous system stimulants such as nicotine;

(l) Expectorants such as guaifenesin; and (m) Anti-inflammatory agents such as isoxicam, and meclophenamic acid.

The medicants may be used alone, in combinations or as an adsorbate such as described in U.S. Pat. 3.085,,942, 4,716,033 or 4,753,800. The use of an absorbate of dextromethorphan HBr on magnesium trisilicate as described in U.S. Pat. 3,085,942 is preferred.

The preferred medicaments include (1) a mixture of the oral decongestants phenylephrine (10.0 mg/piece for adults, 2.5 mg and 5.0 mg per piece for children) phenylpropanolamine HCl (25.0 mg/piece for adults, 12.5 mg/piece and 6.25 mg/piece for children) and pseudoephedrine (60.0 mg/piece for adults, 30 mg/piece and 15 mg/piece for children); (2) antitissuedextromethorphan HBr (10 mg/piece, 20 mg/piece and 30.0 mg/piece for adults and (15 mg/piece, 10 mg/piece, 7.5 mg/piece, 5 mg/piece and 2.5 mg/piece for children) available as the absorbate from Hoffmann LaRoche, Nutley, N.J.; and (3) the antihistamine-chlorpheniramine maleate (4 mg/piece for adults and 2 mg/piece and 1 mg/piece for children).

The colorants useful in the present invention, include the pigments such as titanium dioxide, that may be incorporated in amounts of up to about 1% by weight, and preferably up to about 0.6% by weight. Also, the colorants may include other dyes suitable for food, drug and cosmetic applications, and known as F.D.&C. dyes approved by the FDA. The materials acceptable for the foregoing spectrum of use are preferably water-soluble. Illustrative examples include indigoid dye, known as F.D.&C Blue No. 2, which is the disodium salt of 5,5'-indigotindisulfonic acid. Similarly, the dye known as F.D.&C. Green No. 1, comprises a triphenylmethane dye and is the monosodium salt of 4-[4-nethyl-p-sulfobenzylamino)diphenylmethylene]-[1-(N-ethyl-N-p-sulfoniumbenzyl)-2,5-cyclohexadienimine]. A full recitation of all F.D.&C. and D. & C, and their corresponding chemical structures may be found in the Kirk-Othmer Encyclopedia of Chemical Technology, 3rd Edition in Volume 6, at Pages 561–595, which text is accordingly incorporated herein by reference.

Sugarless water soluble sweeteners may be incorporated into the non-cariogenic confectionery compositions of this invention and include water soluble artificial sweeteners such as soluble saccharin salts, e.g. sodium or calcium saccharin salts, acesulfame K and the free acid forms of saccharin, as well as the dipeptide based sweeteners such as L-aspartyl-L-phenylalanine methyl ester and like materials described in U.S. Pat. 3,492,131.

Other ingredients such as perservatives e.g. butylated hydroxyanisol and the parabens may also be added (at the same time the edible organic acids and flavoring agents are added) to non-cariogenic confectionery compositions of this invention.

GENERAL EXPERIMENTAL

The medicated and non-medicated non-cariogenic confectionery composition of the present invention are characterized as one of four types: soft type (nougats), semi-soft type, semi-hard type and hard type (lozenge). While the texture and hardness of a particular type may vary, we have developed a test using an instrument, Instron model #1122, to quantitatively define each type by the pressure in kilograms required to drive a 0.5 inch (1.27 cm) diameter flat-faced stainless steel circular tablet punch through a confectionery composition sample into a 22/32 donut shaped tablet die having a 11/16 inch diameter hole. As the tablet punch is driven through the confectionery composition sample having a thickness of ¼ to ½ inch, the maximum pressure (P-max) is recorded. The results for each of the four types are recorded hereinbelow in Table II.

TABLE II

| Sample Type | P-Max (Kg/1.27 cm diameter circle) |
| --- | --- |
| Hard Type | >50 |
| Semi-Hard Type | >21–50 |
| Semi-Soft Type | >10 to <21 |
| Soft Type | <10 |

The following examples illustrate the invention. All weight percents, unless otherwise indicated refer to the final cooked confectionery composition.

EXAMPLE 1

Soft-Type Medicated Composition with Dextromethorphan HBr

| Components | % By Weight Added* | % By Weight (after cooking) |
|---|---|---|
| Viscous Liquid Matrix: | 73.900 | 71.150 |
| Semi-Solid Matrix: | 25.599 | 25.257 |
| Other Ingredients: | 0.501 | 0.502 |
| Water | — | 3.091 |
| | 100.00 | 100.00 |

*Excludes Process Water

Ingredients

| Viscous Liquid Matrix (Part A) | % By Weight Added | % By Weight (after cooking) |
|---|---|---|
| Hydrogenated Starch Hydrolysates* | 62.557 | 58.600 |
| Hydrogenated Vegetable Oil | 10.889 | 12.000 |
| Glyceryl Monostearate | 0.454 | 0.500 |

| Semi-Solid Matrix (Part B) | % By Weight Added | % By Weight (after cooking) |
|---|---|---|
| Hydrogenated Starch Hydrolysates* | 17.876 | 16.745 |
| F.D. & C. Red #40 | 0.027 | 0.030 |
| Gelatin | 0.604 | 0.666 |
| Egg Albumen | 0.604 | 0.666 |
| Dextromethorphan HBr 10% adsorbate | 1.361 | 1.500 |
| Magnesium Aluminum Silicate | 0.590 | 0.650 |
| Glycerin | 4.537 | 5.000 |

| Other Ingredients (Part C) | % By Weight Added | % By Weight (after cooking) |
|---|---|---|
| Citric Acid | 0.363 | 0.400 |
| Butylated Hydroxyanisol | 0.002 | 0.002 |
| Flavor | 0.136 | 0.150 |
| Moisture (After Cooking) | — | 3.091 |
| Total | 100.00 | 100.00 |

*Lycasin 85 weight % in water

Procedure

Pre-mix ingredients of viscous liquid matrix in a first pot and cook to 143° C. and hold until used. Premix hydrogenated starch hydrolysate and color of semi-solid matrix and cook to 128° C. and hold until used. Hydrate gelatin with water and add to second pot. Premix all powder ingredients of semi-solid matrix with glycerin and mix until lump free and add to second pot. Admix ingredients in second pot until semi-solid matrix is produced. Add viscous liquid matrix to semi-solid matrix, mix until uniform and cool to 90°–95° C. Add other ingredients of Part C with mixing. Cool and form into pieces.

EXAMPLE 2

Medicated Composition with Phenylpropanolamine HCl Soft Type

| Components | % By Weight Added* | % by Weight (after cooking) |
|---|---|---|
| Viscous Liquid Matrix: | 73.696 | 71.230% |
| Semi-Solid Matrix: | 25.624 | 25.402% |
| Other Ingredients: | 0.680 | 0.752 |
| Water | — | 2.616 |
| Total | 100.00 | 100.00 |

*Excludes process water

| Viscous Liquid Matrix (Part A) | % By Weight Added | % By Weight (after cooking) |
|---|---|---|
| Hydrogenated Starch Hyrolysates* | 62.405 | 58.730 |
| Hydrogenated Vegetable Oil | 10.839 | 12.000 |
| Glyceryl Monostearate | 0.452 | 0.500 |

| Semi-Solid Matrix (Part B) | % By Weight Added | % By Weight (after cooking) |
|---|---|---|
| Hydrogenated Starch Hydrolysates* | 17.854 | 16.800 |
| F.D. & C. Red #40 | 0.018 | 0.020 |
| Gelatin | 0.602 | 0.666 |
| Egg Albumen | 0.602 | 0.666 |
| Phenylpropanolamine HCl | 0.226 | 0.250 |
| Magnesium Aluminum Silicate | 1.806 | 2.000 |
| Glycerin, 99% USP | 4.516 | 5.000 |

| Other Ingredients (Part C) | | |
|---|---|---|
| Citric Acid | 0.452 | 0.500 |
| Butylated Hydroxyanisol | 0.002 | 0.002 |
| Flavor | 0.226 | 0.250 |
| Moisture After Cooking | — | 2.616 |
| Total | 100.00 | 100.000 |

*Lycasin 85 weight percent in water.

Procedure

Admix ingredient in Part A (Viscous Liquid Matrix) and cook, to a temperature of 143° C.; hold the so-formed homogeneous mixture until used. Admix hydrogenated starch hydrolysates and F.D&C Red #40 of Part B and cook to 128° C.; hold the so-formed homogeneous mixture until used. Hydrate gelatin with 2.6 g of water to form a solution and add so-formed solution to admixture of hydrogenated starch hydrolysates and color with mixing until a homogeneous admixture is form. Admix all powder ingredients of Part B and add the so-formed mixture, with stirring, to the glycerin of Part B. Admix until a uniform mixture is formed. Add the uniform mixture and the homogeneous admixture of the ingredients in Part B and admix until the Semi-Solid Matrix is obtained as a homogeneous admixture. Add Part A (Viscous Liquid Matrix) to Part B (Semi-Solid Matrix) and mix until uniform and cool the so-formed uniform admixture to 90° C. Add thereto the other ingredients (Part C). Cool the so-formed homogeneous admixture with mixing to processing temperatures and cut and package.

EXAMPLE 3

Medicated Hard (Lozenge Type) Confectionery Composition

| Components | % By Weight Added* | % By Weight (after cooking) |
|---|---|---|
| Viscous Liquid Matrix | 97.196 | 96.30 |
| Semi-Solid Matrix | 2.629 | 3.00 |
| Other Ingredients | 0.175 | 0.20 |
| Water | — | 0.50 |
| | 100.00 | 100.00 |

*Excludes process water

Ingredients

| Viscous Liquid Matrix (Part A) | % By Weight Added | % By Weight (after cooking) |
|---|---|---|
| Hydrogenated Starch Hyrolysates* | 85.366 | 82.80 |
| Hydrogenated Vegetable Oil | 8.763 | 10.00 |
| Glyceryl Monostearate | 0.438 | 0.50 |

-continued

Medicated Hard (Lozenge Type) Confectionery Composition

| | % By Weight | |
|---|---|---|
| Beeswax | 2.629 | 3.00 |

| Semi-Solid Matrix (Part B) | % By Weight Added | % By Weight (after cooking) |
|---|---|---|
| Hydrogenated Starch Hydrolysates* | 0.876 | 1.00 |
| Glycerin 99% USP | 0.701 | 0.80 |
| Phenylpropanolamine HCl | 0.526 | 0.60 |
| Titanium Dioxide | 0.526 | 0.60 |
| Part C | | |
| Flavor | 0.175 | 0.2 |
| Water (After Cooking) | — | 0.50 |
| Total | 100.00 | 100.00 |

*Lycasin 85 weight % in water.

Procedure

Admix all ingredients of viscous liquid matrix and cook with slow mixing to a temperature of 160° C. to 165° C. until uniform.

Cook hydrogenated starch hydrolysates to 125° C. and hold until used. Admix phenylpropanolamine HCl and titanium dioxide in glycerin. Admix the so-formed mixture with the cooked hydrogenated starch hydrolysates to form semi-solid matrix as homogeneous admixture. Add viscous liquid matrix to the semi-solid matrix. Cool to 90°–95° C. and add flavor. Cool batch and form into lozenges.

EXAMPLE 4

Soft Medicated Confectionery Composition with Calcium Carbonate

| Components | % By Weight Added* | % By Weight (after cooking) |
|---|---|---|
| Viscous Liquid Matrix | 59.439 | 56.320 |
| Semi-Solid Matrix | 40.487 | 40.100 |
| Other Ingredients | 0.074 | 0.080 |
| Water | — | 3.500 |
| Total | 100.00 | 100.000 |

*Excludes process water

| Viscous Liquid Matrix (Part A) | Ingredients % By Weight Added | % By Weight (after cooking) |
|---|---|---|
| Hydrogenated Starch Hydrolysates (Lycasin 85%) | 47.839 | 43.820 |
| Hydrogenated Vegetable Oil | 11.136 | 12.000 |
| Glyceryl Monostearate | 0.464 | 0.500 |
| Semi-Solid Matrix (Part B) | | |
| Hydrogenated Starch Hydrolysate (Lycasin 85%) | 21.834 | 20.000 |
| F.D. & C. Red #40 | 0.017 | 0.018 |
| Egg Albumen | 0.618 | 0.666 |
| Gelatin | 0.618 | 0.666 |
| Glycerin | 4.640 | 5.000 |
| Calcium Carbonate | 12.760 | 13.750 |
| (Part C) | | |
| Flavor | 0.074 | 0.080 |
| Moisture (After Cooking) | — | 3.500 |
| Total | 100.00 | 100.00 |

Pre-mix ingredients of viscous liquid matrix and cook to 143° C. and hold until used. Pre-mix Lycasin 85% hydrogenated starch hydrolysate and color of semi-solid matrix (Part B) and cook to 128° C. and hold until used. Pre-mix gelatin and water add to Part B. Pre-mix remaining ingredients of Part B with glycerin until lump-free and admix with other ingredients of Part B until homogeneous. Add Part A to Part B and mix until uniform. Cool to 90°–95° C. Add flavor thereto and mix until uniform. Cool and form into pieces.

EXAMPLE 5

Mediated Hard (Lorenge Type) Confectionery Composition

| Components | % By Weight Added* | % By Weight (after cooking) |
|---|---|---|
| Viscous Liquid Matrix | 98.003 | 97.215 |
| Semi-Solid Matrix | 1.429 | 1.635 |
| Other Ingredients | 0.568 | 0.650 |
| Water | — | 0.500 |
| | 100.00 | 100.00 |

*Excludes process water

| Viscous Liquid Matrix (Part A) | Ingredients % By Weight Added | % By Weight (after cooking) |
|---|---|---|
| Hydrogenated Starch Hydrolysates* | 87.081 | 84.715 |
| Hydrogenated Vegetable Oil | 10.485 | 12.000 |
| Glyceryl Monostearate | 0.437 | 0.500 |
| Semi-Solid Matrix (Part B) | | |
| Glycerin, Anhydrous | 0.874 | 1.000 |
| Diphenhydromine HCl | 0.546 | 0.625 |
| F.D. & C. Red #40 | 0.009 | 0.010 |
| Other Ingredients (Part C) | | |
| Citric Acid | 0.437 | 0.500 |
| Flavor | 0.131 | 0.150 |
| Moisture | — | 0.500 |
| Total | 100.00 | 100.00 |

Procedure

Admix all ingredients of viscous liquid matrix and cook with slow mixing at 160° C. to 165° C. until uniform.

Premix ingredients of Part B and mix until lump-free and add to cooked viscous liquid matrix. Cool to 90°–95° C. add flavor and citric acid and form into lozenges.

What is claimed is:

1. A medicated non-cariogenic confectionery composition free of cellulosics and graining compounds, said composition comprising:
   (a) a viscous liquid matrix in an amount from about 50% to about 99% by weight of said confectionery composition, said viscous liquid matrix comprising:
      (1) hydrogenated starch hydrolysates in an amount of about 50% to about 95% of said viscous liquid matrix;
      (2) at least one emulsifier in an amount of about 0.5% to about 5% of said viscous liquid matrix;
      (3) at least one edible fat, oil wax, or mixtures thereof in an amount of more than 10% to about 50% by weight of said viscous liquid matrix and more than 10% to about 25% by weight of said composition;
   in homogeneous admixture with
   (b) a semi-solid matrix in an amount from about 50% to about 1% by weight of said confectionery composition, said semi-solid matrix comprising:

(1) hydrogenated starch hydrolysates in an amount of about 0% to about 75% by weight of said semi-solid matrix;
(2) at least one humectant in an amount of about 10% to about 40% by weight of said semi-solid matrix;
(3) at least one viscosity-enhancer in an amount of about 0.5% to about 10% by weight of said semi-solid matrix;
(4) at least one medicament in an amount of from about 0.0001% to about 50% by weight of said semi-solid matrix; and
(5) water in an amount of from about 0.5% to about 8% by weight of said confectionery composition.

2. A confectionery composition of claim 1 containing less than about 65% by weight to 75% by weight of said viscous liquid matrix and more than about 25% by weight to about 65% by weight of said semi-solid matrix.

3. A confectionery composition of claim 1 containing from about 75% to about 84% by weight of said viscous liquid matrix and about 25 to about 16% by weight of said semi-solid matrix.

4. A confectionery composition of claim 1 containing more than about 84% to about 95% by weight of said viscous liquid matrix and less than about 16% to about 5% of said semi-solid matrix.

5. A confectionery composition of claim 1 containing from more than 95% to about 99% by weight of said viscous liquid matrix and less than 5% to about 1% by weight of said semi-solid matrix.

6. A medicated non-cariogenic hard lozenge textured confectionery composition free of cellulosics and graining compound, said composition comprising:
 (a) a viscous liquid matrix in an amount from about 95% to about 99% by weight of said composition said viscous liquid matrix comprising:
  (1) hydrogenated starch hydrolysates;
  (2) at least one emulsifying agent in an amount of about 0.5% to about 5% by weight of said viscous liquid matrix; and
  (3) at least one edible fat, wax, oil or mixtures thereof in an amount of more than 10% to about 26.5% by weight of said viscous liquid matrix and more than 10% to about 25% of said confectionery composition.
in homogeneous admixture with
 (b) a semi-solid matrix in an amount from about 1% to about 5% by weight of said composition said semi-solid matrix comprising:
  (1) hydrogenated starch hydrolysates in an amount of about 0% to about 75% by weight of said semi-solid matrix;
  (2) at least one humectant in an amout of about 10% to about 40% by weight of said semi-solid matrix;
  (3) at least one viscosity-enhancer in an amount of about 0.5% to about 10% by weight of said semi-solid matrix;
  (4) at least one medicament in an amount of from about 0.0001% to about 50% by weight of said semi-solid matrix; and
  (5) water in an amount of from about 0.5% to less than about 1% by weight of said confectionery composition.

* * * * *